US007253898B2

(12) United States Patent
Saikalis et al.

(10) Patent No.: US 7,253,898 B2
(45) Date of Patent: Aug. 7, 2007

(54) SYSTEM FOR DETECTING DROPLETS ON A TRANSLUCENT SURFACE

(75) Inventors: George Saikalis, West Bloomfield, MI (US); Shigeru Oho, Farmington Hills, MI (US)

(73) Assignee: Hitachi, Ltd., Tokyo (JP)

( * ) Notice: Subject to any disclaimer, the term of this patent is extended or adjusted under 35 U.S.C. 154(b) by 193 days.

(21) Appl. No.: 11/096,172

(22) Filed: Mar. 31, 2005

(65) Prior Publication Data
US 2006/0221342 A1 Oct. 5, 2006

(51) Int. Cl.
G08B 21/00 (2006.01)
G01J 1/42 (2006.01)
G01J 1/10 (2006.01)
G01J 1/32 (2006.01)
G01J 1/20 (2006.01)
G01N 21/00 (2006.01)

(52) U.S. Cl. .................. 356/338; 356/221; 356/227; 356/229; 250/205; 250/201.1; 340/602

(58) Field of Classification Search ............. 356/239.1, 356/4, 5, 7, 8, 335–343, 432, 221, 226, 227, 356/223, 230; 250/227.25, 559.4, 573, 208.1, 250/205, 201.1, 206; 340/601, 602; 345/8
See application file for complete search history.

(56) References Cited

U.S. PATENT DOCUMENTS

| 4,859,867 | A | * | 8/1989 | Larson et al. .............. 307/10.1 |
| 5,477,332 | A | * | 12/1995 | Stone et al. ................ 356/613 |
| 5,703,568 | A | * | 12/1997 | Hegyi ......................... 340/602 |
| 6,262,407 | B1 | * | 7/2001 | Teder ........................... 250/205 |
| 6,353,392 | B1 | * | 3/2002 | Schofield et al. ............ 340/602 |
| 6,603,137 | B2 | * | 8/2003 | Hochstein .................... 250/573 |
| 2004/0046103 | A1 | * | 3/2004 | Stam et al. ............... 250/208.1 |
| 2004/0144911 | A1 | * | 7/2004 | Stam et al. ............... 250/208.1 |
| 2005/0035926 | A1 | * | 2/2005 | Takenaga et al. ............... 345/8 |
| 2006/0163458 | A1 | * | 7/2006 | Reime ..................... 250/227.25 |

OTHER PUBLICATIONS

A review of the automotive market for rain sensors: 2005 edition—corporate user licence (download); Oct. 2004. Just-auto.com.
Christine Fuhr, Schott Glas. Sensor.
Optical Sensors Performance Issues History; Rain Sensors: An Overview, OEDED, Copyright 2001-2004, Opto-Electronic Design, Inc.
Yet2.com; TechPak Rain detector, Copyright 1999-2004, yet2.com, Inc.
Rain-sensing Wipers TRW Automotive.
Worldstyling.com, Refresh your engine; Rain Sensor, 2002-2005 Worldstyling.com.
Coyle, S. What Technicians Need to Know about Rain Sensors., Making Waves! Copyright 2004 Independent Glass Association.

* cited by examiner

Primary Examiner—Tarifur Chowdhury
Assistant Examiner—Daniel Cartoon
(74) Attorney, Agent, or Firm—Gifford, Krass, Sprinkle, Anderson & Citkowski, P.C.

(57) ABSTRACT

A system which detects droplets on a translucent surface having a camera which, upon activation, acquires an image of a portion of the surface. A radiation source, upon activation, illuminates the portion of the translucent surface while a control circuit selectively activates both the camera and the radiation source. A processor receives a captured image from the camera and, through image processing, generates an output signal representative of the number of droplets on the portion of the translucent surface.

27 Claims, 3 Drawing Sheets

SYSTEM FOR DETECTING DROPLETS ON A TRANSLUCENT SURFACE

BACKGROUND OF THE INVENTION

I. Field of the Invention

The present invention relates generally to a system for detecting droplets on a translucent surface.

II. Description of Material Art

There are previously known systems for detecting droplets on a translucent surface. These previously known systems are typically used in the automotive industry for detecting raindrops on the windshield of a vehicle. Upon detection of the raindrops, the vehicle's windshield wipers are activated.

These previously known raindrop detectors in the automotive industry typically comprised one of two different types. In a first type, a light emitting diode (LED) having an output radiation emission in the infrared range was arranged in the automotive vehicle to direct the infrared emission towards a portion of the windshield. Reflected infrared radiation was then detected by an infrared detector. This reflected infrared radiation changes whenever raindrops are present on the windshield and these changes are detected by the infrared detector.

One problem associated with this previously known LED raindrop detector, however, is that the raindrop detector was unable to differentiate between raindrops and other marks on the windshield, such as debris, smudges, and the like. Consequently, when the raindrop detector was utilized to control the activation of the windshield wipers, these previously known systems were prone to activate the windshield wiper system when such activation was not desired. Furthermore, windshield coatings, such as ultraviolet coatings, often interfered with the operation of the detector.

In the second type of raindrop detector, an ultrasonic transmitter was effectively coupled to the windshield and, similarly, an ultrasonic receiver coupled to the windshield at a position spaced from the transmitter. In the event of the presence of raindrops on the windshield, the raindrops tended to dampen the ultrasonic vibration and such dampening is detected by the ultrasonic receivers.

This previously known raindrop detector, however, is disadvantageously costly to implement in the automotive industry. Furthermore, since the ultrasonic vibration transmitter necessarily involved a mechanical interface with the windshield, such mechanical interfaces were prone to failure.

A still further disadvantage of these previously known systems is that such systems were unable to detect the magnitude or number of raindrops.

SUMMARY OF THE PRESENT INVENTION

The present invention provides a system for detecting droplets on a translucent surface which overcomes all of the above-mentioned disadvantages of the previously known devices.

In brief, the system of the present invention comprises a camera which, upon activation, acquires an image of at least a portion of the translucent surface and then generates an output signal representative of that image. In the preferred embodiment of the invention, the camera comprises a CCD camera, although other types of cameras may be utilized without deviation from the spirit of the invention.

A radiation source is also mounted relative to the windshield so that, upon activation, the radiation source illuminates the portion of the translucent surface which is subject to the image captured by the camera. The radiation source may be either invisible, such as an infrared radiation source, or visible light. However, in the event that visible light is used, preferably the visible light radiation source is activated for a period of time sufficiently small so as to be undetectable by a human eye.

The system further includes a processor which receives the camera output signal as an input signal and, through image processing, generates an output signal representative of the number of droplets on the portion of the translucent surface. Although different means may be utilized to implement the image processing, in the preferred embodiment of the invention, the processor captures two sequential images. One image is captured by the camera when the radiation source is deactivated. Conversely, the other image is captured when the radiation source is activated. Consequently, by processing an image equal to the difference between the two sequential images, this differential image will contain clusters, if present, corresponding to droplets on the translucent surface. Binarization of those clusters will, in turn, provide a signal representative of the magnitude, i.e. the number and/or quantity, of raindrops on the portion of the translucent surface.

BRIEF DESCRIPTION OF THE DRAWING

A better understanding of the present invention will be had upon reference to the following detailed description, wherein like reference characters refer to like parts throughout the several views, and in which.

DETAILED DESCRIPTION OF A PREFERRED EMBODIMENT OF THE PRESENT INVENTION

Figure 1:
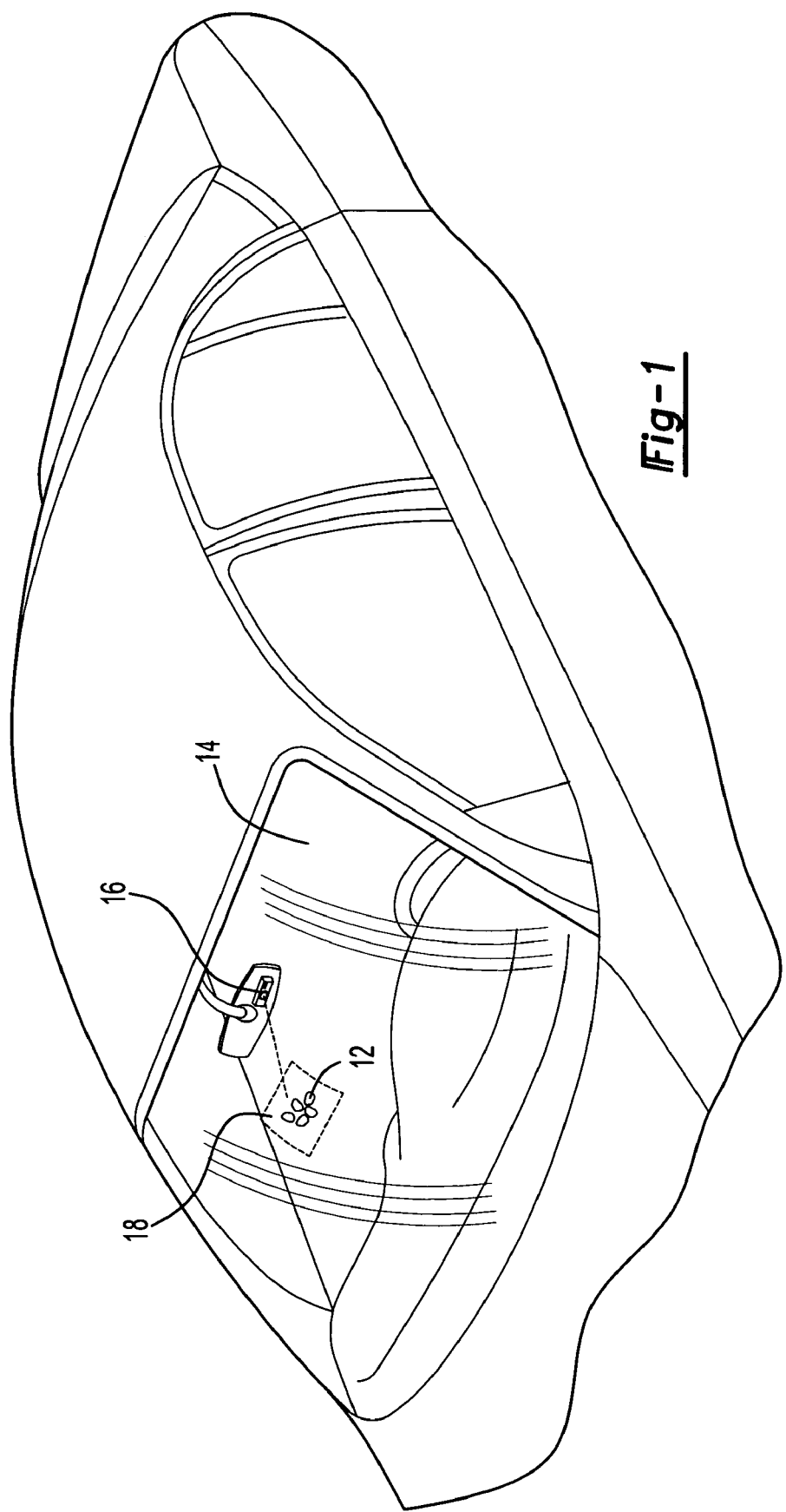
FIG. 1 is an elevational view illustrating a preferred embodiment of the present invention.
Figure 2:
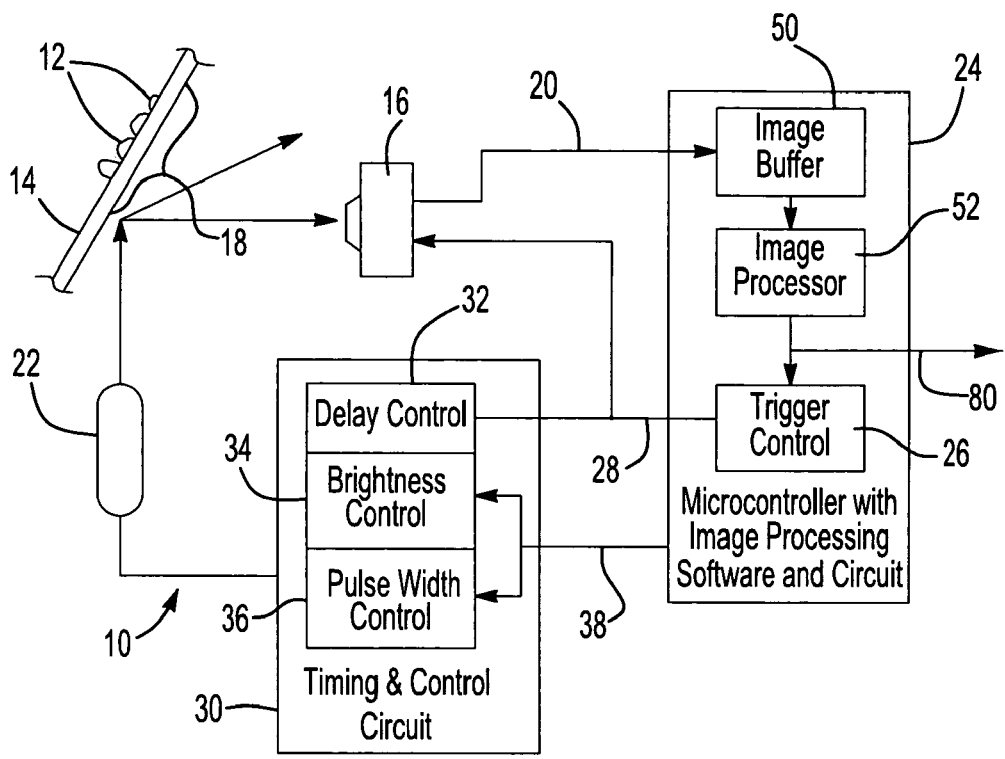
FIG. 2 is a block diagrammatic view illustrating a preferred embodiment of the present invention.

With reference first to FIGS. 1 and 2, a preferred system 10 of the present invention for detecting droplets 12 on a translucent surface 14 is shown. For example, the translucent surface 14 may comprise a windshield of an automotive vehicle while the droplets 12 comprise raindrops, snowflakes, slush and/or the like.

A camera 16 is positioned relative to the translucent surface 14 so that, when activated, the camera 16 captures an image of at least a portion 18 of the translucent surface 14. The camera 16 generates a digital signal on its output 20 representative of the captured image. Furthermore, the camera 16 is preferably a charge coupled device (CCD) camera, although other types of cameras may be used without deviation from the spirit or scope of the invention.

Still referring to FIGS. 1 and 2, a radiation source 22 is also associated with the windshield 14 so that, when activated, the radiation source 22 illuminates the portion 18 of the windshield 14. Preferably, the radiation source 22 comprises a light emitting diode (LED).

The radiation source 22 may operate in either the invisible range, such as the infrared range, or in the visible range of light. In any event, both the camera 16 and radiation source 22 are selected such that the camera 16 is sensitive to the wavelength of radiation from the radiation source 22.

An electronic control circuit 24 includes a trigger control 26 which produces an output signal on its output 28 to activate the camera 16. The control circuit 24 also activates the radiation source 22 through a radiation source control circuit 30.

Figure 4:
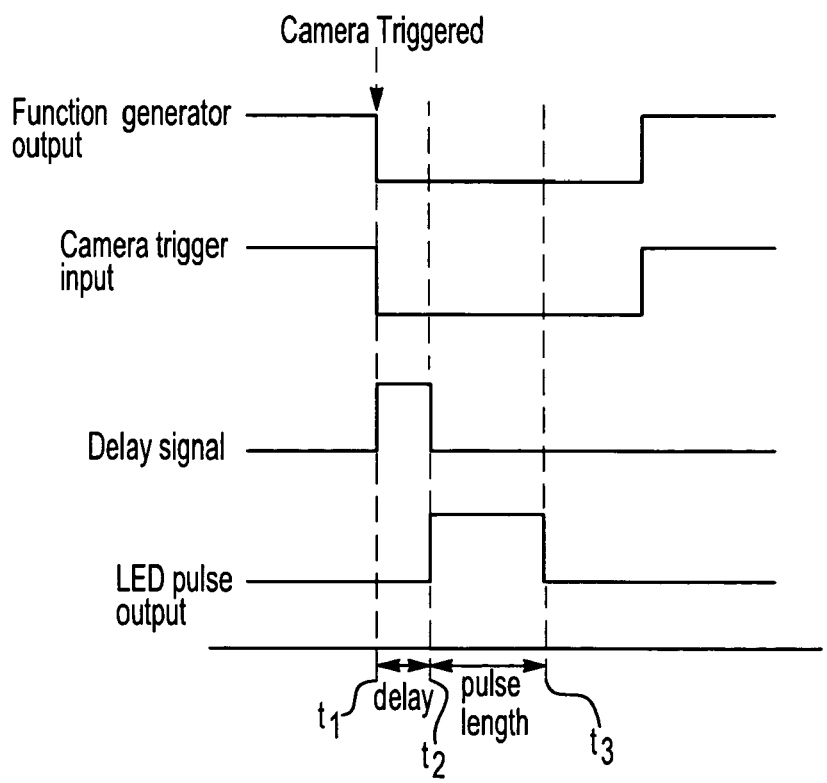
FIG. 4 is a timing diagram illustrating the operation of the preferred embodiment of the present invention.

With reference now to FIGS. 2 and 4, the radiation-controlled circuit 30 includes a delay control 32 which delays activation of the radiation source 22 for a predetermined time period following receipt of the trigger pulse from the trigger control 26. Thus, as best shown in FIG. 4, assuming that the trigger control circuit 26 generates a trigger pulse on its output 28 at time $t_1$, the delay control 32 delays activation of the radiation source 22 until time $t_2$. The delay between time $t_1$ and time $t_2$ allows the camera 26 to "set up" before acquiring the image of the windshield portion 18. The activation period for the radiation source 22 is depicted between times $t_2$ and $t_3$ in FIG. 4.

Referring now particularly to FIG. 2, the radiation control circuit 30 also includes a brightness control 34, as well as a pulse width control 36 which varies both the brightness of the radiation source 22 when activated, as well as the width of the activation pulse, i.e. between time $t_2$ and $t_3$ in FIG. 4, in response to control-signals from the control circuit 24 on output line 38. In some instances, for example, it would be desirable to increase the brightness of the radiation source 22 in response to a magnitude of ambient light. Likewise, adjustment of the pulse width of the radiation source 22 may be desirable to improve system performance in view of changing ambient light, as well as other environmental factors.

Still referring to FIG. 2, the camera 16, upon activation, transmits a digital image of the windshield portion 18 to an image buffer 50 in the control circuit 24. The output from the image buffer 50 is, in turn, coupled as an input signal to an image processor 52. The image processor 52 preferably includes a microprocessor which is programmed to process two sequential images. One of the sequential images comprises an image of the windshield portion 18 while the radiation source 22 is deactivated. Conversely, the other of the two sequential images is acquired by the camera 16 while the radiation source 22 is activated.

In the well-known fashion, the presence of droplets 12 on the front surface of the windshield 14 will vary the reflectivity of the windshield portion 18 and create a dark spot on the acquired image. Consequently, the number of droplets 12, or at least an approximate number of droplets 12, on the windshield portion 18 can be determined by the image processor 52 by creating an image equal to the difference between the first and second sequential image. The image representing the difference between the two sequential images can easily be determined by exclusive ORing the two images which also automatically eliminates smudges and other marks on the windshield portion 18.

Figure 3:
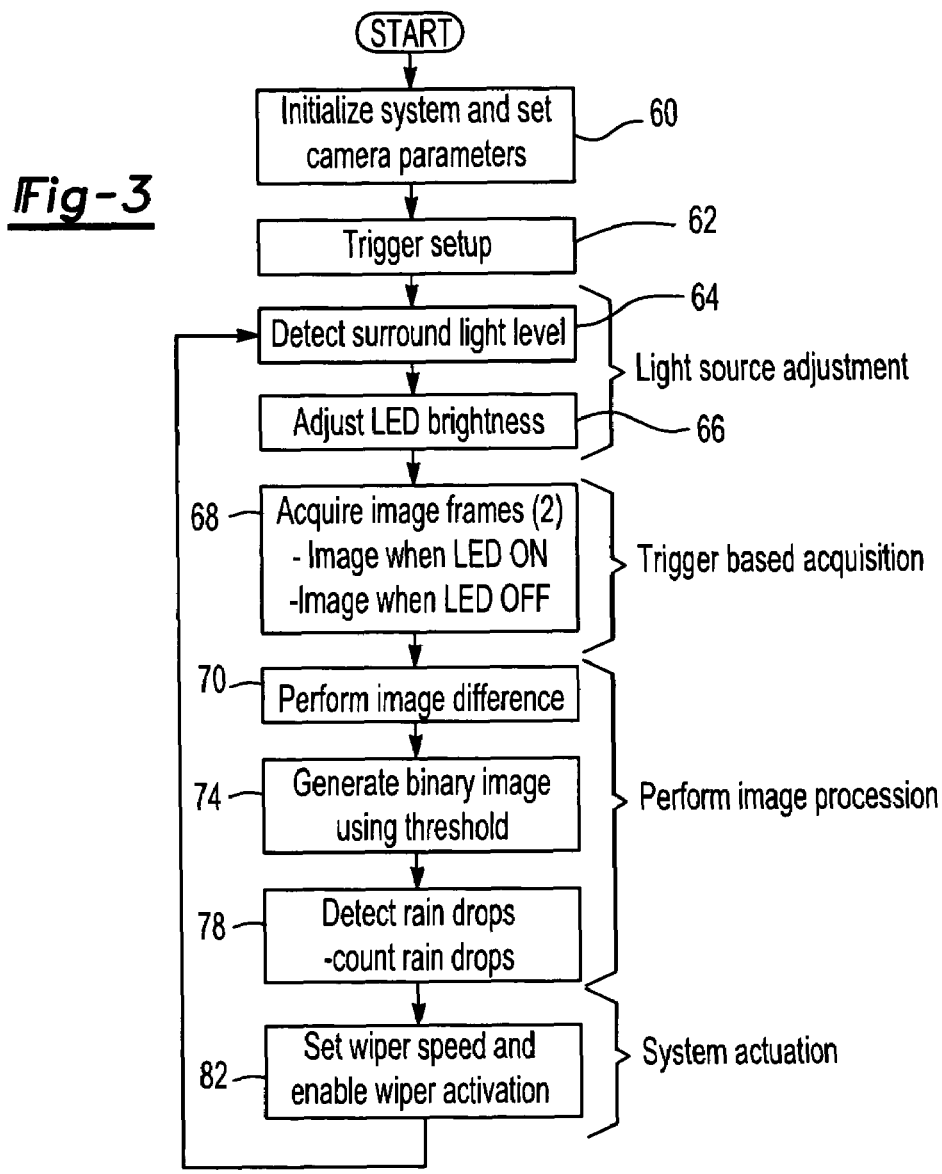
FIG. 3 is a flowchart illustrating the operation of the preferred embodiment of the present invention.

With reference to FIG. 3, a preferred embodiment of the operation of the image processor 52 is there shown in greater detail. At step 60, the entire system is initialized and the camera parameters set. Step 60 then proceeds to step 62 where the trigger control 26 is initiated to begin the two sequential image captures by the camera 16.

Step 62 then proceeds to step 64 where the system 10 detects the ambient light level at the windshield portion 18. Any conventional means, such as a visible light detector, may be utilized to detect the ambient light at the windshield portion 18. Furthermore, if desired, the camera 16 may also be used initially as a detector of the ambient light at step 64. Step 64 then proceeds to step 66 where an output signal from the control circuit 24 on line 38 is generated to a brightness control 34 to vary the brightness of the radiation source 22.

Step 66 then proceeds to step 68 where the image processor 52 acquires two sequential images from the camera 16. In one of the images, the radiation source 22 is deactivated by the radiation control circuit 30 or the control circuit 24 while, conversely, in the other image, the radiation source 22 is activated by the radiation control circuit 30 or control circuit 24. It does not matter whether the radiation source 22 is activated during the first sequential image or second sequential image.

Figure 5:
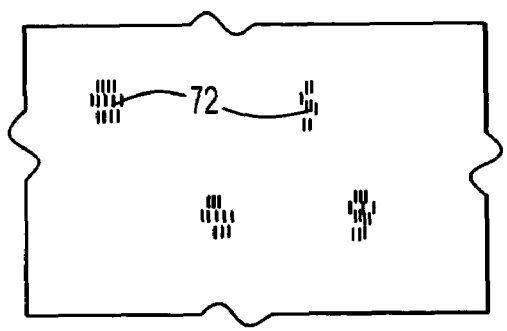
FIG. 5 is an exemplary image of droplets on a translucent surface.

Step 68 then proceeds to step 70 where the processor 52 provides an image difference of the two sequentially captured images. An exemplary image difference is illustrated in FIG. 5 in which four clusters 72, each representing a single droplet 12, are illustrated as an exemplary image difference. Step 70 then proceeds to step 74.

Figure 6:
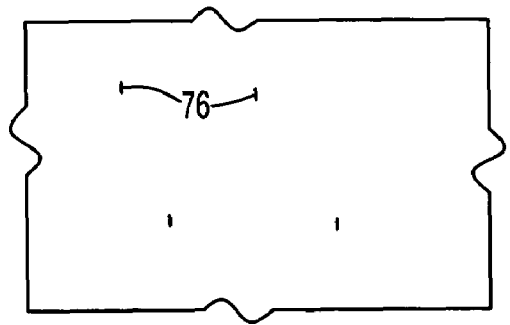
FIG. 6 is a binarized image of FIG. 5.

At step 74, each cluster 72 (FIG. 5) representing a raindrop is subjected to a binarization which reduces each cluster 72 to a single pixel 76, as shown in FIG. 6. Any conventional method may be utilized to reduce the droplet images 72 (FIG. 5) into a single pixel 76 (FIG. 6) without deviation from the spirit or the scope of the invention. Such methods include, for example, the Sobel, Roberts, Laplace, Prewitt and Canny methods.

Following binarization of the image difference, the binary numbers generated at step 74 are merely counted at step 78 and the image processor 52 generates an output signal on its output 80 (FIG. 2) representative of the magnitude, e.g. number, of droplets 12 on the windshield 14.

In one exemplary embodiment, step 78 then proceeds to step 82 where the processor 52 enables the windshield wipers and sets the windshield wiper speed as a function of the number of raindrops counted on the windshield portion 18. In order to prevent jerking or erratic activation of the windshield wipers, the processor preferably utilizes a rolling average of the number of counted droplets 12 on the windshield 14 when adjusting the speed of the windshield wipers.

After the processor 52 activates the windshield wipers and sets the windshield wiper speed at step 82, step 82 branches back to step 64 where the above process is reiterated.

As previously described, the radiation source 22 may be either invisible, such as infrared radiation, or visible light. However, in the event that the radiation source 22 emits radiation in the range of visible light, the radiation source control circuit preferably controls the activation of the radiation source 22 to pulses which are too short to be detected by a human eye. For example, it is known that light pulses no longer than a few microseconds in length are not detectable by the human eye. Alternatively, a shield may be used to mask the light pulses from the user.

Although in the preferred embodiment of the invention, the image processor 52 counts the number of droplets 12 on the windshield 14 and generates a signal representative of the magnitude of the droplets, the processor 52 may alternatively or additionally be programmed to process the size of the droplets 12. For example, edge detection techniques applied to the exemplary image shown in FIG. 5 may be utilized to determine the magnitude of the droplets 12. Alternatively, the magnitude may be determined as a function of the proportionate area of the windshield portion covered by the droplets. In any case, the larger magnitude is indicative of a heavier rainfall, and will preferably result in an increase of the windshield wiper speed.

From the forgoing, it can be seen that the present invention provides a simple and yet highly effective method for detecting droplets on a translucent surface, such as raindrops on a windshield. Having described our invention, however, many modifications thereto will become apparent to those skilled in the art to which it pertains without deviation from the spirit of the invention as defined by the scope of the appended claims.

We claim:

1. A system for detecting droplets on a translucent surface comprising:
    a camera which, upon activation, acquires an image of at least a portion of the translucent surface and generates an output signal representative of said image,
    a radiation source which, upon activation, illuminates the at least a portion of the translucent surface,
    a control circuit which selectively activates said camera and said radiation source,
    a processor which receives said camera output signal and, through image processing, generates an output signal representative of the magnitude of droplets on the at least a portion of the translucent surface,
    wherein said radiation source comprises a visible light source, and
    wherein during activation of said radiation source, said control circuit activates said radiation source for a sufficiently short period of time so as to be undetectable to a human eye.

2. The invention as defined in claim 1 wherein said control circuit activates said camera to produce a first and a second sequential image, said control circuit deactivating said radiation source during one of said first and second sequential image and activating said radiation source during the other of the first and second sequential image, said processor output signal representing the difference between said first and said second sequential image.

3. The invention as defined in claim 1 wherein said control circuit iteratively activates said camera and said radiation source.

4. The invention as defined in claim 1 wherein said camera comprises a charge coupled device.

5. The invention as defined in claim 4 wherein said control circuit activates said radiation source a predetermined time period after activation of said camera.

6. The invention as defined in claim 1 wherein said control circuit comprises a brightness control circuit which varies the brightness of the radiation source.

7. The invention as defined in claim 1 wherein said control circuit comprises a pulse width circuit which varies the duration of activation of said radiation source.

8. The invention as defined in claim 1 wherein said processor generates an output signal representative of the size of the droplets in the at least a portion of the translucent surface.

9. The invention as defined in claim 1 wherein said magnitude of droplets comprises the number of droplets on said portion of the translucent surface.

10. The invention as defined in claim 1 wherein said magnitude of droplets comprises the proportion of area coverage of said droplets on said portion of said translucent surface.

11. For use in conjunction with a translucent windshield and a variable speed windshield wiper which, when activated, wipes droplets from the windshield, a system for detecting droplets on the windshield comprising:
    a camera which, upon activation, acquires an image of at least a portion of the windshield and generates an output signal representative of said image,
    a visible light radiation source which, upon activation, illuminates the at least a portion of the windshield,
    a control circuit which selectively activates said camera and said radiation source,
    a processor which receives said camera output signal and, through image processing, generates an output signal representative of the magnitude of droplets on the at least a portion of the translucent surface,
    a wiper speed control circuit which receives said processor output signal and varies the speed of the windshield wiper as a function of said processor output signal,
    wherein said control circuit comprises a brightness control circuit which varies the brightness of the radiation source, and
    wherein during activation of said radiation source, said control circuit activates said radiation source for a sufficiently short period of time so as to be undetectable to a human eye.

12. The invention as defined in claim 11 wherein said control circuit activates said camera to produce a first and a second sequential image, said control circuit deactivating said radiation source during one of said first and second sequential image and activating said radiation source during the other of the first and second sequential image, said processor output signal representing the difference between said first and said second sequential image.

13. The invention as defined in claim 11 wherein said radiation source comprises a light source.

14. The invention as defined in claim 11 wherein said radiation source comprises an infrared radiation source.

15. The invention as defined in claim 11 wherein said control circuit iteratively activates said camera and said radiation source.

16. The invention as defined in claim 11 wherein said camera comprises a charge coupled device.

17. The invention as defined in claim 16 wherein said control circuit activates said radiation source a predetermined time period after activation of said camera.

18. The invention as defined in claim 11 wherein said control circuit comprises a pulse width circuit which varies the duration of activation of said radiation source.

19. The invention as defined in claim 11 wherein said processor generates an output signal representative of the size of the droplets in the at least a portion of the windshield.

20. The invention as defined in claim 11 wherein said magnitude of droplets comprises the number of droplets on said portion of the translucent surface.

21. The invention as defined in claim 11 wherein said magnitude of droplets comprises the proportion of area coverage of said droplets on said portion of said translucent surface.

22. The invention as defined in claim 11 wherein said processor generates said output signal representative of a rolling average of the magnitude of droplets on said portion of said translucent surface.

23. A method for detecting droplets on a translucent surface comprising the steps of:
    acquiring an image of at least a portion of the translucent surface,
    generating an output signal representative of said image,
    illuminating the at least a portion of the translucent surface with a pulse of visible light having a duration undetectable to a human eye, image processing said image to generate an output signal representative of the magnitude of droplets on the at least a portion of the translucent surface.

24. The invention as defined in claim 23 wherein said image acquiring step further comprises the steps of acquiring two sequential images wherein only one of said images is acquired during said illuminating step, and wherein said image processing step comprises the step of determining differences between said two sequential images.

25. The invention as defined in claim 23 and further comprising the step of varying the brightness of said illuminating step.

26. The invention as defined in claim 23 wherein said image processing step comprises the step of determining the size of droplets on the translucent surface.

27. The invention as defined in claim 23 wherein said image processing step comprises the step of determining the number of droplets on the translucent surface.

* * * * *